(12) United States Patent
Chen et al.

(10) Patent No.: US 9,730,769 B2
(45) Date of Patent: *Aug. 15, 2017

(54) RELEASE AGENT RECEPTACLE

(71) Applicant: Align Technology, Inc., San Jose, CA (US)

(72) Inventors: Jennifer C. Chen, San Francisco, CA (US); Li-Hung Su, Foster City, CA (US); Chunhua Li, Cupertino, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/558,418

(22) Filed: Dec. 2, 2014

(65) Prior Publication Data
US 2015/0093713 A1    Apr. 2, 2015

Related U.S. Application Data

(63) Continuation of application No. 12/011,942, filed on Jan. 29, 2008, now Pat. No. 8,899,976.

(51) Int. Cl.
| | |
|---|---|
| *A61C 7/08* | (2006.01) |
| *A61C 7/00* | (2006.01) |
| *A61C 19/06* | (2006.01) |
| *A61K 49/00* | (2006.01) |
| *A61C 19/04* | (2006.01) |

(52) U.S. Cl.
CPC .................. *A61C 7/08* (2013.01); *A61C 7/00* (2013.01); *A61C 19/063* (2013.01); *A61C 19/066* (2013.01); *A61K 49/00* (2013.01); *A61C 19/04* (2013.01)

(58) Field of Classification Search
CPC .......... A61C 7/08; A61C 19/063; A61C 19/04
See application file for complete search history.

(56) References Cited

U.S. PATENT DOCUMENTS

| | | |
|---|---|---|
| 3,503,127 A | 3/1970 | Kasdin et al. |
| 3,533,163 A | 10/1970 | Kirschenbaum |
| 3,813,781 A | 6/1974 | Forgione |
| 3,885,310 A | 5/1975 | Northcutt |

(Continued)

FOREIGN PATENT DOCUMENTS

| | | |
|---|---|---|
| CN | 1867317 A | 11/2006 |
| WO | 9858596 A1 | 12/1998 |

(Continued)

OTHER PUBLICATIONS

Partial International Search Report from international application No. PCT/US2008/005680, dated Aug. 18, 2008, 5 pp.
Benson et al., "Highly Porous Polymers," American Laboratory, pp. 1-12, Apr. 2003.
Brannon-Peppas, "Biomaterials: Polymers in Controlled Drug Delivery," Medical Devicelink, Medical Plastics and Biomaterials Magazine, 19 pp., Nov. 1997.

(Continued)

*Primary Examiner* — Ralph Lewis
(74) *Attorney, Agent, or Firm* — Brooks, Cameron & Huebach, PLLC

(57) ABSTRACT

The present disclosure includes method, system, apparatus, and indicator embodiments. One apparatus includes an appliance for placement over one or more teeth and a release agent receptacle including an outer portion provided on appliance surface, an inner portion provided within the outer portion, and one or more apertures formed in the outer portion.

20 Claims, 5 Drawing Sheets

(56) References Cited

U.S. PATENT DOCUMENTS

| | | | |
|---|---|---|---|
| 4,039,653 | A | 8/1977 | DeFoney et al. |
| 4,255,138 | A | 3/1981 | Frohn |
| 4,278,087 | A * | 7/1981 | Theeuwes ............ A61K 9/0004 424/405 |
| 4,450,150 | A * | 5/1984 | Sidman .................... A61D 7/00 252/62.53 |
| 4,629,424 | A | 12/1986 | Lauks et al. |
| 4,741,700 | A | 5/1988 | Barabe |
| 4,818,542 | A | 4/1989 | De Luca et al. |
| 4,968,251 | A | 11/1990 | Darnell |
| 5,194,003 | A | 3/1993 | Garay et al. |
| 5,645,420 | A | 7/1997 | Bergerson |
| 5,651,671 | A | 7/1997 | Seay et al. |
| 5,911,576 | A | 6/1999 | Ulrich et al. |
| 5,975,893 | A | 11/1999 | Chishti et al. |
| 5,980,246 | A | 11/1999 | Ramsay et al. |
| 5,993,413 | A | 11/1999 | Aaltonen et al. |
| 6,099,303 | A | 8/2000 | Gibbs et al. |
| 6,607,382 | B1 | 8/2003 | Kuo et al. |
| 7,553,157 | B2 | 6/2009 | Abolfathi et al. |
| 8,899,976 | B2 * | 12/2014 | Chen .................... A61C 7/00 433/6 |
| 2006/0068353 | A1 | 3/2006 | Abolfathi et al. |
| 2006/0115782 | A1 | 6/2006 | Li et al. |
| 2006/0115785 | A1 | 6/2006 | Li et al. |
| 2008/0118882 | A1 | 5/2008 | Su |

FOREIGN PATENT DOCUMENTS

| | | |
|---|---|---|
| WO | 02058583 A1 | 8/2002 |
| WO | 2005114183 A1 | 12/2005 |
| WO | 2006060547 A2 | 6/2006 |

OTHER PUBLICATIONS

Landgraf et al., "Polymer Microcarrier Exhibiting Zero-Order Release," Drug Delivery Technology, vol. 3, No. 1, pp. 1-14, 2003.

Lawrence, "Salivary Markers of Systemic Disease," Journal of Canadian Dental Association Clinical Practice, vol. 68, No. 3., pp. 170-174, Mar. 2002.

Middleton et al., "Materials: Synthetic Biodegradable Polymers as Medical Devices," Medical Plastics and Biomaterials Magazine, MPB Article Index, 14 pp., 1998.

Nishanian et al., "Oral Fluids as an Alternative to Serum for Measurement of Markers of Immune Activation," Clinical and Diagnostic Laboratory Immunology, vol. 5, No. 4, pp. 507-512, Jul. 1998.

Sigma-Aldrich Co., "Tutorial, Biocompatible/Biodegradable Materials," http://www.signmaldrich.com/area_of_interest/organic_inorganic_chemistry/materials_science/biocompatible_, undated, 3 pp.

Svec et al., "Molded Rigid Monolithic Porous Polymers: An Inexpensive, Efficient, and Versatile Alternative to Beads for the Design of Materials for Numerous Applications," Ind. Eng. Chem. Res. 1999, 38, pp. 34-48.

Unknown, Excerpt from a reference on water-soluble polymers, date unknown, 2 pp.

Van Der Eijk et al., "Paired measurements of quantitative hepatitis B virus DNA in saliva and serum of chronic hepatitis B patients: implications for saliva as infectious agent," Journal of Clinical Virology, vol. 29, pp. 92-94, 2004.

First Office Action from related Chinese patent application No. 201410060043, dated Dec. 21, 2015, 6 pp.

Extended Search Report from related European Patent Application No. 16191809, dated Feb. 10, 2017, 7 pp.

* cited by examiner

RELEASE AGENT RECEPTACLE

RELATED APPLICATIONS

The present application is a continuation of U.S. patent application Ser. No. 12/011,942, filed Jan. 29, 2008, which will issue as U.S. Pat. No. 8,899,976 on Dec. 2, 2014, which is a continuation in part (CIP) of U.S. patent application Ser. No. 11/799,979, filed May 3, 2007, now U.S. Pat. No. 7,854,609, which was a continuation in part (CIP) of U.S. patent application Ser. No. 10/949,717, filed on Sep. 24, 2004, now U.S. Pat. No. 7,553,157, the disclosure of which is incorporated in its entirety herein by reference.

BACKGROUND

The present disclosure is related to systems and methods for providing release agent receptacles.

As noted in commonly owned U.S. Pat. No. 6,607,382 entitled "Methods and systems for concurrent tooth repositioning and substance delivery," the content of which is incorporated herewith, the repositioning of teeth may be accomplished with the use of a series of removable elastic positioning appliances such as the Invisalign® system available from Align Technology, Inc., the assignee of the present disclosure. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances including new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, the content of these documents are incorporated by reference for all purposes.

The appliance is effective in repositioning teeth when it is placed over the patient's teeth. In some implementations, it is desirable to wear these appliances most of the day (e.g., all of the time except when eating and maintaining oral hygiene, such as by brushing or flossing). Although easy and convenient to wear, the patient may not wear the appliance as prescribed by the treatment professional. Extended removal of the appliance, for any reason beyond what is recommended, interrupts the treatment plan and lengthens the overall period of treatment. Since the appliance is removable by the patient, the treatment professional has to rely on the patient to comply with the prescription.

Additionally, there may be many variables and differences in each patient's oral environment and, therefore, one type of compliance indicator may not likely be enough to last for a desired period of wear in every person. Some examples of the factors that may change the wear rate include an amount of saliva produced, one or more tooth anatomies or locations, a composition of saliva, an analysis of sleep habits of a patient, an amount of liquid consumption, and one or more types of liquid consumed, among other criteria. These factors can make the analysis of compliance based upon a wear indicator difficult due to the different wear rates that different people may have.

SUMMARY

The present disclosure includes method, system, apparatus, and indicator embodiments. One apparatus includes an appliance for placement over one or more teeth and a release agent receptacle including an outer portion provided on appliance surface, an inner portion provided within the outer portion, and one or more apertures formed in the outer portion.

Another apparatus embodiment includes an apparatus for monitoring orthodontic treatment compliance includes an appliance adapted to be worn over one or more teeth; and a compliance indicator mounted on the appliance or teeth to indicate compliance. Advantages of some embodiments of the system include one or more of the following. Some such apparatus embodiments provide better data for communicating device compliance with patients, including: increased patient knowledge and recall of appliance usage; increased compliance in wearing the dental appliance, and increased patient satisfaction as a result. The apparatus provides a channel of self-monitoring for the patient. The apparatus also reduces patient's anxiety levels without requiring verbal or written instructions since device usage is self-evident. The treatment professional also has better information on patient progress during the treatment.

DESCRIPTION

Figure 1:
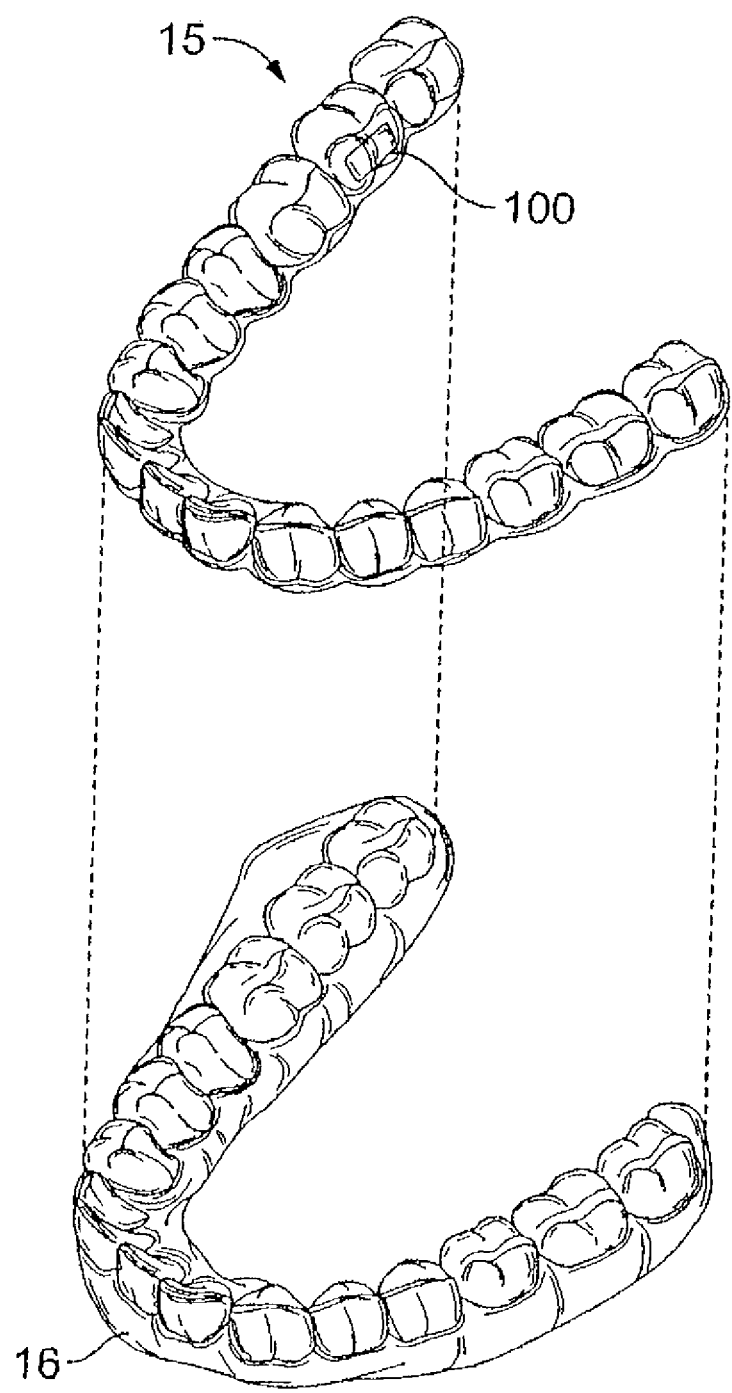
FIG. 1 shows an exemplary compliance indicator.

FIG. 1 shows an exemplary removable appliance 15 adapted to fit over teeth on a jaw 16. A usage indicator 100 can be mounted on one tooth or on the appliance 15 to indicate patient compliance.

In one implementation, the indicator 100 can be a coat on a tooth or an appliance with a chemical agent. Alternatively, the indicator 100 can be an electrical agent, optical agent or mechanical agent that indicates appliance wearage. In some embodiments, the indicator agent is inactive until contact with liquid or moisture. Alternatively, release of the agent can be stimulated by liquid or moisture. Thus, in one case, upon wearing, oral fluids activates the agent and allows the agent to seep out and indicate compliance. Alternatively, oral fluids such as saliva, among others, can seep in to activate the agent to indicate compliance.

In another embodiment, the appliance can release a coloring agent to the oral environment when the appliance is worn over the teeth. Such mechanisms may include a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may include the agent present in or on a carrier or binder which promotes adhesion or attachment to the appliance and/or which creates a matrix from which the agent can be released by diffusion or dissolution. In some embodiments, the agent is dissolved in the carrier or binder. In this case, the agent may be provided in powder or similar form and dissolved in a liquid solvent. The result may be a solution which may be applied to a surface of the shell, typically by spraying, painting, and/or dipping, to form a coating or film. When the repositioning appliance is placed over the patient's teeth, the compliance indicating agent may then be released from the coating to the oral environment. Release may be due to activation or deactivation of the carrier or any other releasing mechanism, such as by enzymes or proteins in oral fluids. Or release may be due to degradation of the carrier by contact with, for example, oral fluids. In some cases, the binder or carrier may evaporate upon application to the layer to the surface leaving the agent behind. In these cases, the agent may be released in a similar fashion as when the agent is directly attached to the surface, as described above. It may be appreciated that any suitable agent, such as fluoride materials, antibiotics or other drugs or medications, vitamins, bleaching materials, and/or breath fresheners, may be delivered to the oral environment in this manner.

In another embodiment, the agent is encapsulated or suspended in the layer. A common material for suspension of an agent is a semisolid material, such as a gel, jelly, or putty. Such a material may be applied to a surface of the shell by spraying, painting, and/or dipping to form a coating or film. Here, as in all cases, suspension is not limited to a scientific definition and may refer to any situation in which a carrier holds, contains, supports, or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials, and breath fresheners, may be delivered to the oral environment in this manner.

Another common material for encapsulation or suspension of an agent is a controlled-release material. Thus, the layer may be of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly, or putty, as described above, these materials may also be provided as a solid material which is attached to the polymeric shell of the repositioning appliance. One type of controlled-release material includes a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's oral fluids will activate the release or degrade the carrier material to release the agent. It may be appreciated that the agent may be released by a combination of any of the release methods.

In a further embodiment, the polymeric shell of the repositioning appliance itself includes a controlled-release material containing the agent. In this case, at least a portion of a polymeric shell is formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material, or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing mechanism coupled to at least some of the repositioning appliances includes a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing mechanism is designed for a single delivery period, the appliance may be worn throughout the prescribed repositioning period and then disposed of. If the releasing mechanism is designed for multiple delivery periods, the reservoir may be replenished with the agent to be released any number of times throughout the prescribed repositioning period. It may be appreciated that any agent, particularly fluoride materials, antibiotics, bleaching materials, and breath fresheners, may be delivered to the oral environment in this manner.

In some instances, it may be desirable to change a visual characteristic of the polymeric shell of an oral appliance. Such appliances include a polymeric shell having a cavity shaped to be removably placeable over the teeth and a material on or within the shell that changes a visual characteristic of the shell. Such a change is typically in response to a change in the environment. In some cases, the visual characteristic is a color, such as green, red, or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37 degree C.) to room temperature (25 degree C.). Similarly, the dye may change color when the appliance is rinsed with cool water.

The appliance can be used to provide an intra-oral drug delivery system. In addition to the agents described above, other compounds can be used as well. For example, a drug coated appliance can be used to deliver desensitizing medication to sensitive teeth. The drug substance can simply be a small amount of the active ingredient in a desensitizing toothpaste or gel, such as Sensodyne®. The desensitizing agent is dispersed throughout the surface of the appliance and is delivered, at a substantially constant rate, to the patient's sensitive teeth for a relatively extended period of time.

Although the appliance may be pre-loaded with the agent and ready for use upon removal from any packaging, appliances that are not pre-filled or pre-loaded may require loading prior or immediately prior to placing the appliance over the teeth. Loading may include placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may include placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also include adhering a rate controlling material containing the agent to a surface of the appliance prior to placing the appliance over the teeth. Such a material may include a polymer matrix membrane which may be removably or permanently adhered to the polymeric shell of the appliance in desired areas for delivery of the agent. And finally, loading may include absorbing the agent into a porous material on or within the appliance immediately prior to placing the appliance over the teeth.

Mechanisms for releasing the agent may include a number of embodiments, including any such mechanisms previously described. Typically, mechanisms for releasing the agent includes a layer including the agent, as previously described, and coupling includes adhering the layer to at least a portion of a surface of the appliance. When the layer consists essentially of the agent, adhering may involve coating, spraying, dipping, or painting the agent on the surface of the appliance. Thus, a pre-formed appliance may simply be coated with the agent prior to insertion in the patient's mouth. When the layer includes an agent present in or on a carrier or binder, adhering may involve attaching the carrier or binder a surface of the appliance. Similarly, when the agent is encapsulated in the layer, the layer may be attached to the surface of the appliance. The layer may include a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution of the agent, allowing the appliance to absorb or adsorb the agent at a particular time.

In addition, the sheet may be pre-formed to a shape adapted for fitting against the surface of the appliance or a surface of the teeth or gingiva. For example, the sheet may be pre-formed to reflect the shape of the surface of one or more teeth or the gingiva, particularly along the gingival margin. The preformed sheet may then be held against that surface when the sheet is coupled to the appliance and the appliance is placed over the teeth. Coupling may involve any mechanism of attaching the sheet to the appliance. In particular, the pre-formed sheet may further include an adhesive layer which may provide bonding of the sheet to the surface of the appliance.

The material to make to the appliance of FIG. 1 can be supplemented with additional fillers such as electrically conducting fillers, magnetic fillers, illuminating fillers, piezoelectric fillers, and/or light sensitive fillers. The material properties of the appliance made with or without these additional fillers such as modulus, electrical resistance, material permeability, and birefringence (degree of orientation of the material or stress), illuminating patterns or patterns under special light sources may change after the appliance is worn over time, as these properties are altered due to changes in structure, organization, and/or spatial spacing between the fillers. For example, it is well established that electrical conductivity of filled composites scales with filler volume concentration according to percolation theory. Therefore, mechanical deformation or thermal expansion of the non-conductive polymer matrix will lead to increased average inter-filler spacing, or decreased filler volume concentration, and consequently decreased electrical conductivity. Examples of electrically conductive fillers include metals, graphite, electrically conductive polymers, semiconductors, and superconductors. These changes in properties can be used as an indicator for compliance and can be diagnosed by instrumentation. Similarly, separation of conductive fillers will also lower thermal conductivity, which can also be measured by instrumentations. If the fillers have magnetic behavior in the presence of external stimulation, such as diamagnetics (Cu, Au, Ag, etc.) and paramagnetics (e.g. Al, Cr, Na, Ti, Zr, etc.); or exhibit intrinsic magnetic properties, such as ferromagnetics (Fe, Co, Ni, etc.), antiferromagnetics (e.g. MnO), and ferromagnetics ($MFe_2O_4$), then separation of the filler spacing due to mechanical deformation of the polymer matrix can also lead to decreases in magnetic properties above the Curie temperature. Mechanical deformation of composites with illuminating fillers, such as those that exhibit luminescence, fluorescence, or phosphorescence, will result in decreased illumination intensity. Bending deformation or displacement of piezoelectric fibers can result in electrical potentials which can be either measured, or used to activate other electrically driven indicators (e.g. low power LED light). Fillers with optical properties which depend on external electric field, for example those that shift their absorption coefficients in the UV, IR, or visible spectrum can also serve as indicator of matrix deformation.

Figure 2A:
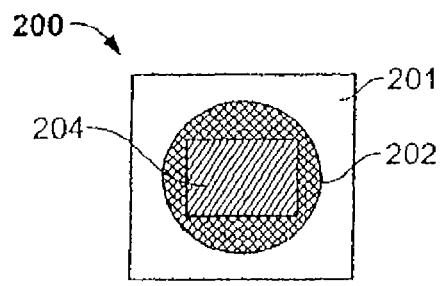
FIGS. 2A-2C show a first embodiment of the compliance indicator of FIG. 1.

Referring now to FIG. 2A, an embodiment of an indication attachment device 200 is shown. The indication attachment device 200 includes a polymer well 201, and the well 201 includes a semi-permeable membrane 202. The membrane 202 allows a two-way flow between the well 201 and an interface to the oral environment. Within the well 201, a material 204 such as a dyed material is provided.

In some embodiments, the dyed material 204 is a releasable material, such as dyed poly(vinylsiloxane) (PVS) material. The PVS material is used to hold the dye, and the membrane 202 can be a cellulose acetate membrane. Those skilled in the art will understand that other releasable materials such as polyether, polyurethane, ethyl vinyl acetate can also be manipulated to result in the teachings of this patent.

In another embodiment, the well material 204 can be an enzyme or a reactor that reacts with enzymes from the oral fluids. When oral fluids or enzyme from the oral fluids enters the well, the material 204 reacts with the enzyme to provide an indication. Alternatively, a pH indicator can be used as the material 204. In yet another embodiment, the membrane 202 can be silicon instead of PVS.

In another embodiment, the polymer can be water-soluble polymer that includes water-soluble polymers, lightly cross-linked hydrogels, and high molecular weight with hydrogen bonding plastics that demonstrate some limited water resistance. Natural-based water-soluble polymers include starch, starch-oxided, cellulose, cellulose-alkoxylated, cellulose-carboxyalkylated, chitin, chitosan, pectins, hyaluronic acid, proteins, and lignin. Water-soluble polymers can also be created from synthetic raw material through polymerization by addition/vinyl, condensation, and ring-opening. Examples of these types of polymers are poly(vinyl alcohol), polyesters, and poly(alkylene oxides). The hydrolytic instability of biodegradable polymers is advantageous because the presence of the oral fluids will facilitate the degradation of the polymer.

Figure 2B:
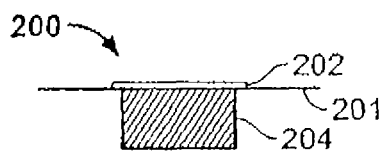
Figure 2C:
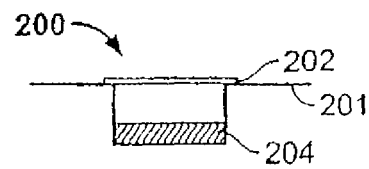

Referring now to FIG. 2B, a cross-sectional view of the compliance indication attachment device (compliance indicator) 200 is shown. As viewed therein, the membrane 202 is positioned above the polymer well, chamber, or housing 201 with the releasable material and or dye 204 enclosed therein. As shown in FIG. 2C, after a predetermined period of time, for example two weeks, a portion of the dyed PVS material 204 has seeped out causing a change in appearance of the indication attachment device. The dye is released while the PVS stays inside the device. In this case, a color change can occur or alternatively, the volume of the material has changed, in this case it has reduced in size.

In some embodiments, the compliance indicator 200 has a clear, tooth-colored, or esthetically pleasing polymer reservoir well, chamber, or housing 201. A transparent or translucent semi-permeable membrane 202 separates the content within the reservoir chamber 201 from the external oral environment. The content(s) within the reservoir chamber 201 depends on the overall strategy to monitor compliance. In one implementation, contents diffuse out from the reservoir chamber 201, through the membrane 202, into the external environment. For example: the content can be an FDA approved visible dye which diffuses from the chamber 201, through the membrane 202, and into the external oral environment. When the content is emptied, the content color diminishes in brightness and value. Colorants that are permitted for direct addition to human food by the US FDA include annatto extract, beta-carotene, beet powder, canthaxanthin, caramel color, carrot oil, cochineal extract (carmine); cottonseed flour, fruit juice, paprika, riboflavin, saffron, turmeric, vegetable juice, FD&C Blue No. 1 (brilliant blue) and No. 2 (indigotine), FD&C Green No. 3 (fast green FCF), FD&C Red No. 3 (erythrosine) and No. 40 (allura red), FD&C Yellow No. 5 (tartrazine) and No. 6 (sunset yellow). Other food colorants such as those found at FDA's Center for Food Safety and Applied Nutrition website: http://www.cfsan.fda.gov/.about.dms/col-toc.html can be used as well.

In another implementation, matter from the external environment diffuse in, and reacts with the contents 204 within the reservoir chamber 201. For example, glucose molecules from the external environment diffuse through the membrane 202, and reacts with enzymes inside the content and the resultant enzymatic products interact with other reactants inside the content to cause color change. As more glucose molecules diffuse in, content color increases in brightness and value. A convenient enzyme system is glucose oxidase and horseradish peroxidase. The first enzyme, glucose oxidase, catalyzes the oxidation of glucose to form gluconic acid and hydrogen peroxide. Hydrogen peroxide then reacts with 3-3,5,5'-tetramethylbenzidine (TMB) under catalytic action of horseradish peroxidase to convert yellow TMB to green. Other colorants, such as potassium iodide (green to brown) may also be used. These enzymes can be immobilized within the chamber. The rate of reaction, and hence color change, can be controlled by selecting the permeability of the membrane 202, the concentration of reactants inside the chamber 201, and the method of delivery. The rate of reaction or concentration of the glucose molecules can also be detected through spectroscopy or other analytical testing. Test results will correlate with compliance to treatment.

Figure 3A:
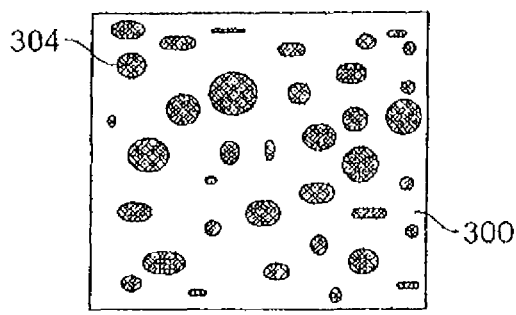
FIGS. 3A-3B show a second embodiment of the compliance indicator of FIG. 1.
Figure 3B:
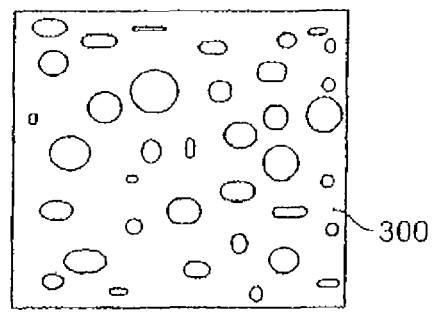

Referring now to FIGS. 3A and 3B, another embodiment of an indication attachment device is shown. In the embodiment of FIG. 3A, a porous polymer material is provided on a sheet 300. The polymer material is disposed on the sheet 300 as one or more containers 304. The container 304 may be a well as disclosed above in the discussion of FIGS. 2A-2C. After a predetermined period of usage, the polymer material changes appearance, for instance, changes either to the color or the size as shown in FIGS. 2B-2C. Other implementations can include colored polymers (both thermoplastic and thermoset materials) and composites utilizing the same compliance mechanism as the porous polymer material.

The compliance indicator of FIGS. 3A-3B thus can be a dye encapsulated in a polymer which is released in the presence of oral fluids. The dye can be colorants that react with the oral fluids and that are released from the polymer. The polymer can be porous polymer such as monolithic porous polymer (currently used in chromatography), PVS, a high internal phase emulsion (HIPE polymer currently used in drug release), or any macroporous polymer. The dyed polymer will be constructed into a small button that can be bonded to the exterior of the aligner. The amount of dye loss will correspond with the amount of time the aligner was in use. The pore size of the polymer and the particle size of the dye will affect the rate of diffusion of dye from the button to the oral fluids environment and depending on compliance needs, these factors can be controlled.

Porous polymers are prepared by adding "porogens" during the polymerization process of resins. Porogens are soluble in the monomer but insoluble in formed polymers. As polymerization occurs, pores are formed in the spaces where porogens are found. The newest type of porous polymers is known as "high internal phase emulsions" ("HIPE"). HIPE structures have pore diameters much larger than previous porous materials which had only pore diameters in the angstroms.

Another porous polymer is the monolithic porous polymer currently being used in chromatography. The polymerization of this rigid macroporous polymer takes the shape of the mold, usually a column, into which the monomers and porogens are poured into. Generally, the pore volume is nearly equal to the amount of porogens added into the monoliths.

Figure 4A:
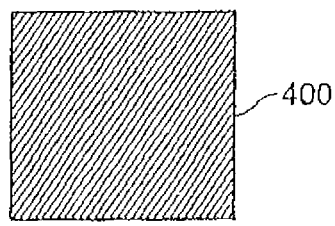
FIGS. 4A-4B show a third embodiment of the compliance indicator.
Figure 4B:

Referring now to FIGS. 4A and 4B, a button embodiment of an indication attachment device 400 is shown. In this embodiment, a biodegradable polymer material is attached to either a tooth or a dental appliance. After a certain period of use, the polymer material either changes shape or size or color, and as shown in FIG. 4B, the volume of the biodegradable polymer material is subsequently reduced. In some embodiments, the button is a biodegradable polymer button. The button can be molded from a biodegradable polymer and bonded to the exterior of the aligner. The button will have a predetermined degradation period such as a two week degradation period in the constant presence of oral fluids. Potentially the polymer can be colored for a more visible indication of the degradation of the button. The size and material will determine the degradation period of the button. However, other factors such as brushing of the aligner and rinsing will have to be taken into consideration when determining the optimal degradation time of the button.

The degradation products often define the biocompatibility of a polymer. Synthetic biodegradable polymers are favored over natural ones because of reliability of raw materials. The following is a list of common biodegradable polymers: polyglycolide (PGA), polylactide (PLA), l-lactide (LPLA), poly(dl-lactide) (DLPLA), poly(.epsilon.-caprolactone) (PCL), polydioxanone (PDO), poly(glycolide-co-trimethylene carbonate) (PGA-TMC), and polyorthoesters.

Figure 5:
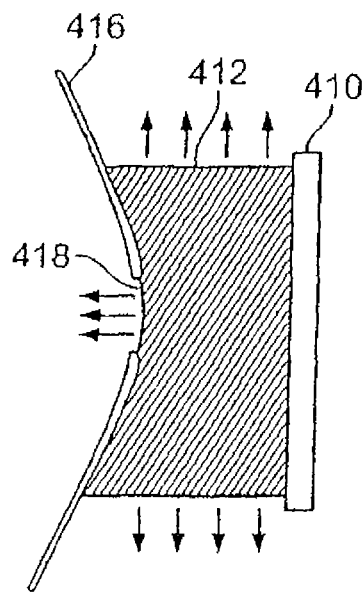
FIG. 5 shows a fourth embodiment of the compliance indicator.

FIG. 5 shows yet another embodiment of an indication attachment device. In this embodiment, an appliance 416 receives an adhesive dye matrix 412. The matrix 412 is sealed either at one end or both ends using a backing film 410. The material in the matrix 412 can be released on the sides between the appliance 416 and the film 410 or between the two backing films. An opening 418 may be provided in the appliance 416 and one side of the backing film to facilitate dye release. In one implementation, a transdermal patch may be applied in a manner similar to drug releasing transdermal patches. Instead of embedding and releasing drug in the adhesive matrix, a dye is released and the mechanism for dye loss is moisture (oral fluids). In one implementation, appliance wear compliance is indicated by the color of the adhesive layer: the more dye lost, the longer the wear time.

Figure 6:
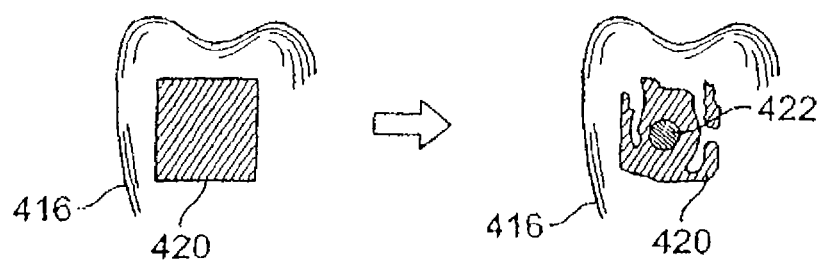
FIG. 6 shows a fifth embodiment of the compliance indicator.

FIG. 6 shows yet another embodiment where the wear indication is achieved through a water dissolvable film. In this embodiment, an opaque water soluble film 420 is positioned to cover one or more colored areas, regions, spots, or dots 422 on an appliance or on a tooth. The film can be a protective coating that can be used to protect the indicator (e.g., dot) from wear, such as from brushing teeth, etc. Since these appliances may be intended to be used for most of the day (e.g., 20+ hours), in many situations, protection of the indicator may be helpful in determining compliance.

In some embodiments, the protective coating can be removable and can be used to protect the indicators before and/or during application to an appliance or to one or more teeth. Such embodiments can also improve the accuracy of compliance analysis, in some instances.

In some embodiments, the dots 422 can be a series of colored dots with varying thicknesses of film 420 and each exposed color corresponds to a different amount of appliance wear time. In the embodiment where the dots 422 are imprinted on the appliance, the film 420 is layered onto the surface of the appliance. The mechanism of releasing dye is moisture (oral fluids).

Figure 7:
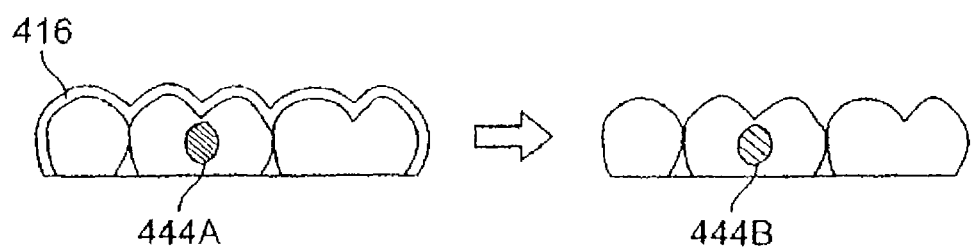
FIG. 7 shows a sixth embodiment of the compliance indicator.

FIG. 7 shows another embodiment where a tooth attachment 444A is made with a dye-releasing composite. The dye-releasing composite 444A bonded to a tooth will be covered by an appliance 416. Over time, the dye-releasing composite 444A has a reduced or no color loss compared to the loss for a dye on an uncovered tooth attachment 444B. The color of the attachment will correspond to the amount of aligner wear. The mechanism of dye releasing is moisture (oral fluids) in this embodiment.

In yet other implementations, a diagnostic indicator can be provided. The diagnostic indicator is similar in device construction to the compliance indicator, and utilizes the inwards diffusion strategy, where biochemical analytes from the external environment are allowed to diffuse through the membrane to react with the contents within the reservoir chamber. Thus, biomarkers from the external environment diffuse through the membrane, and react with reagents inside the content to directly or indirectly induce color change or chemical change that can be quantified through human eye or laboratory testing or computerized vision systems. As more biomarkers diffuse into the diagnostic indicator, the content color changes, for example increases in brightness and value. Possible biomarkers include enzymes, pH, glucose, salt, oral film, plaque, microorganisms that may exist in the oral cavity and amount of oral fluids.

Figure 8:
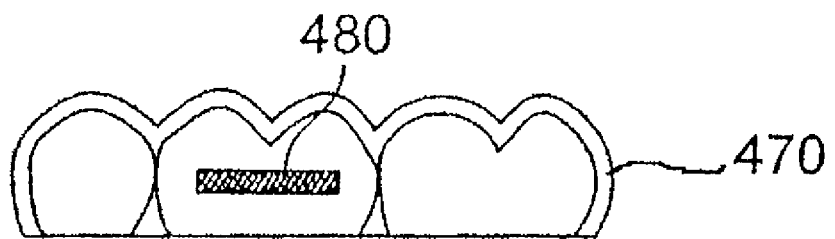
FIG. 8 shows a seventh embodiment of the compliance indicator.

In the embodiment shown in FIG. 8, the compliance indicator can be a time temperature indicator 480. The indicator 480 is intra-orally placed in the mouth (either directly on a tooth or on an appliance 470) and provides an indication of the time the indicator has been at a preselected intra-oral temperature environment.

Figure 9:
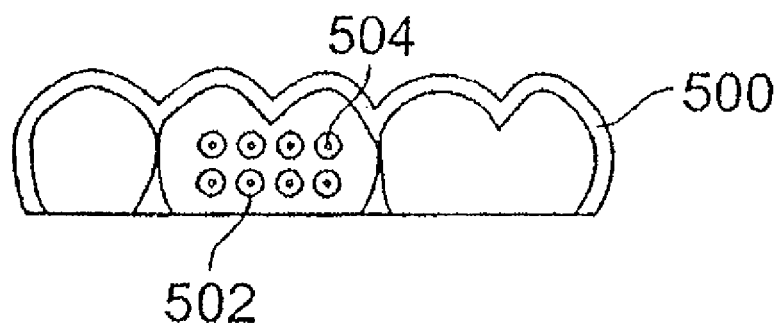
FIG. 9 shows an eighth embodiment of the compliance indicator.

In yet another embodiment shown in FIG. 9, a plurality of brushes 502 having a colored fiber 504 is positioned on the appliance 500. As the brush 502 is gradually eroded by wearing the appliance 500, a dye, or other suitable indicia of wear in the fiber 504 is exposed for visual detection by a human or by a machine. Alternatively, the brushes 502 can be placed on one or more teeth instead of on the appliance 500.

In yet another embodiment, the compliance indication is human readable by changing physical or mechanical or visual properties that are readily observable by a human. In other embodiment, the compliance indication is machine readable. For instance, in one embodiment that alters the electrical characteristics of an appliance during wearing of the appliance, an electrical measurement can be made by a computer for detecting compliance. In another embodiment that uses biomarkers, a computer with biomarker sensor can be used with suitable computer program to detect compliance. In yet another embodiment, a color change can be detected by a computer vision program to detect compliance.

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

Portions of the system and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission, or display devices.

Figure 10:
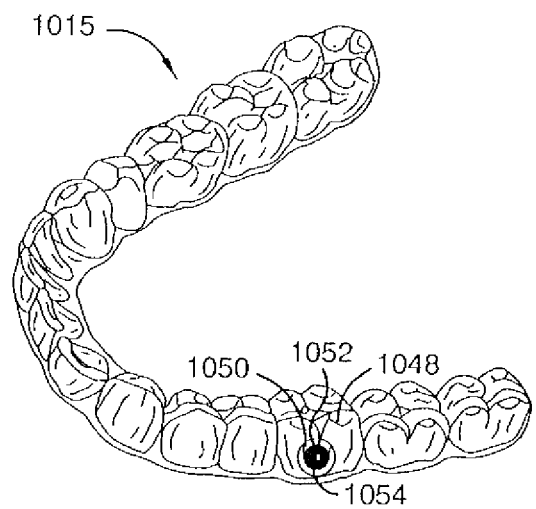
FIG. 10 shows an appliance having a release agent receptacle according to an embodiment of the prevent disclosure.

FIG. 10 shows an appliance having a release agent receptacle according to an embodiment of the prevent disclosure. FIG. 10 illustrates that a release agent receptacle can be provided (e.g., placed on, manufactured on) on an appliance 1015 such as an aligner for dental treatment, among other types of dental appliances.

In the embodiment of FIG. 10, the release agent receptacle includes an outer portion 1050 provided on appliance surface 1048, with an inner portion 1052 provided within the outer portion 1050, and an aperture 1054. In some embodiments, the inner portion 1052 can be encapsulated within the outer portion 1050.

In various embodiments, an outer portion can, for example, be provided by a polymer and/or curable material (e.g., ultra violet-curable acrylic) among other types of suitable materials. Other examples of suitable materials include, but are not limited to materials such as an ultra violet-acrylic material, an epoxy material, a urethane material, a rubber material, an ethylene vinyl acetate material, an elastomer material, a plastic material, and/or a silicone material, among other suitable material types.

The inner portion 1052 can be utilized as an active portion of the release agent receptacle, wherein the inner portion has an active ingredient such as a dye, pigment, or other indicator material and/or materials that can be used for treatment. In such embodiments, these receptacles can be referred to as compliance indicators so long as they have the functionality of compliance indication.

In some embodiments, the active ingredient can be embedded in a polymer or other suitable type of material. Polymers and other such materials can be useful in such embodiments, for example, because the rate at which the active ingredient is released or leaches out may be controlled by the type of polymer or other such material the active ingredient is embedded in.

In order to facilitate the release of the material in the inner portion of the release agent receptacle, one or more apertures 1054 can be provided through the outer portion 1050 and to the surface of the inner portion 1052. In some embodiments, the aperture 1054 can be provided through the outer portion 1050, through some or all of the inner portion 1052 and/or into or through the outer portion 1050 that is proximate to the surface 1048 of the appliance 1015. In various embodiments, the size and/or shape of the one or more apertures can be adjusted to change the amount, speed, direction, and/or other characteristics of the release of the material from the inner portion 1052.

The one or more apertures can be formed in any suitable manner. For example, in some embodiments, the aperture can be drilled through the cured adhesive to allow moisture, more specifically saliva, to interact with an active ingredient in the inner portion. In some embodiments, the aperture can be formed during the formation of the other portions of the appliance (e.g., in some embodiments where the appliance and release agent receptacle are formed integrally).

The active ingredient can be any suitable ingredient for use in oral indication, diagnosis, and/or treatment and can be released in any suitable manner. For example, in some embodiments, the mechanism of dissolution of the active material and release can be through moisture from the mouth of the patient. A suitable example of an active ingredient is FD&C blue dye in the case of the compliance indicator, however, such and example should not be viewed as limiting on the embodiments of the present disclosure.

Figure 11:
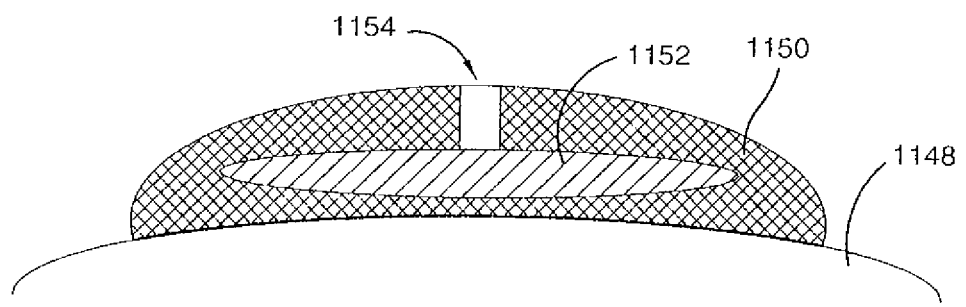
FIG. 11 shows a cut-away side perspective view of the receptacle embodiment of FIG. 10.

In some embodiments, as illustrated in FIG. 11, the release agent receptacle can be formed with or integrally bonded to the surface of the appliance. In some embodiments, the release agent receptacle can be adhered to or non-integrally bonded to the surface of the appliance.

In such embodiments, a bonding material can be utilized that can, for example, be composed of a biocompatible pressure-sensitive adhesive (e.g., acrylic, silicone, and/or polyisobutene) which can allow for adhesion of the release agent receptacle to the aligner surface, or other suitable surfaces.

In some embodiments, the compliance indicator can be a wear indicator. As discussed herein, use of various materials can be utilized to provide a number of different wear rates. A wear material can, for example, be composed of a water-soluble polymer (e.g., high molecular weight polyvinyl alcohol) mixed with a FD&C (FDA certified) "aluminum lakes" dye which allows for leaching of the color over a period of time, among other materials Although the wear rates of these indicators may not be standardized from one patient to another, the wear rates of these indicators can be predetermined with respect to each other. In such embodiments, indicators of various wear rates with respect to each other can be utilized.

Such wear indicators can be used as compliance indicators or as treatment disbursement apparatuses (e.g., for the disbursement of agents as described herein) as the wearable material wears during use of the appliance to which it is associated. This wear can, for example be produced through interaction with moisture as discussed above.

Such wear rates can be established, for example, by exposing the wear indicator to a uniform reactant (e.g., a material that causes the indicator to change). The periods of change to the indicators can be measured and can, therefore, be used to set the amount of expected change with respect to the other indicators similarly tested.

For instance, a dye may have a particular wear pattern over time, which may be uniform or may increase, decrease, or otherwise change over time. Such rates can be determined and the usage of the appliance calculated based upon where the wear indication provided by the indicator is on the wear pattern of the particular material being used in the indicator.

Some examples of the type of wear that can be used to determine the wear rate of the wear layer can determined based upon one of the factors selected from the group including amount of saliva produced, one or more tooth anatomies or locations, a composition of saliva, an analysis of sleep habits of a patient, an amount of liquid consumption, and one or more types of liquid consumed, among other criteria. The analysis of compliance can be accomplished in any suitable manner based upon the information provided by the initial indicators.

FIG. 11 shows a cut-away side perspective view of the release agent receptacle embodiment of FIG. 10. In the embodiment of FIG. 11, the release agent receptacle includes an outer portion 1150 provided on appliance surface 1148, with an inner portion 1152 provided within the outer portion 1150, and an aperture 1154. In some embodiments, the inner portion 1152 can be encapsulated within the outer portion 1150 with the aperture being formed after the encapsulation has been done.

In some embodiments, the appliance 1148 can include one or more of the release agent receptacles mounted on the appliance 1148 to indicate compliance and/or the amount of treatment disbursement that has been done by demonstrating a change in at least one characteristic of the release agent receptacle. The changed characteristic can, for example, be a color, shape, and/or size, among others. In some embodiments, compliance and/or disbursement can be indicated by an absence of a change.

In order to facilitate the release of the material in the inner portion of the release agent receptacle, one or more apertures 1154, as discussed above, can be provided through the outer portion 1150 and to the surface of the inner portion 1152. In some embodiments, the aperture 1154 can be provided through the outer portion 1150, through some or all of the inner portion 1152, and/or into or through the outer portion 1150 that is proximate to the surface 1148 of the appliance 1115.

Some embodiments may also continue the aperture through a portion or all of the thickness of the appliance. Such embodiments may allow for material from the inner portion 1152 to interact with the teeth and/or gingiva of the patient that are positioned on or near the aperture 1154 within the appliance 1115. In various embodiments, the size and/or shape of the one or more apertures can be adjusted to change the amount, speed, direction, and/or other characteristics of the release of the material from the inner portion 1152.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, although films or appliances have been disclosed as mechanisms for compliance measurement, droplets can be used to deliver the compliance indicating substances to the patient as well.

Other embodiments for compliance indication can be used as well. Whereas particular embodiments of the present invention have been described herein for purposes of illustration, it will be evident to those skilled in the art that numerous variations of the details may be made without departing from the invention as defined in the appended claims.

We claim:

1. A dental release agent receptacle, comprising:
    an outer portion including a bottom surface configured to be coupled to an outer surface of an individual tooth aperture of an appliance, the bottom surface configured to have a perimeter smaller than a perimeter of the outer surface of the individual tooth aperture, the bottom surface of the outer portion shaped to fit against the outer surface of the individual tooth aperture;
    an inner portion encapsulated within the outer portion; and
    an aperture through a top surface of the outer portion of the release agent receptacle allowing for fluid communication from the inner portion and out of the dental release agent receptacle, wherein the top surface is smaller than the bottom surface, and wherein the inner portion and the outer portion are in fluid communication by the aperture only.

2. The dental release agent receptacle of claim 1, wherein the inner portion is a wear indicator, wherein a type of wear that determines a wear rate of the wear indicator is determined based upon a factor selected from the group including:
    amount of saliva produced;
    one or more tooth anatomies or locations;
    a composition of saliva;
    an analysis of sleep habits of a patient;
    an amount of liquid consumption; and
    one or more types of liquid consumed.

3. The dental release agent receptacle of claim 2, wherein the inner portion includes a wear material to provide the wear indicator.

4. The dental release agent receptacle of claim 3, wherein the wear material includes a water-soluble polymer mixed with a dye material to allow for leaching of the dye over a period time.

5. The dental release agent receptacle of claim 1, wherein the inner portion is utilized as an active portion of the release agent receptacle, wherein the inner portion has an active ingredient.

6. The dental release agent receptacle of claim 5, wherein the active ingredient is embedded in a polymer.

7. The dental release agent receptacle of claim 5, wherein the active ingredient is selected from the group of materials including a dye material and a pigment material.

8. The dental release agent receptacle of claim 1, wherein the aperture is provided through the outer portion and through a portion of the inner portion.

9. The dental release agent receptacle of claim 1, wherein an active ingredient is embedded in a material of the dental release agent receptacle in which a rate at which the active ingredient is released is controlled by the type of material that the active ingredient is embedded in.

10. The dental release agent receptacle of claim 1, wherein the inner portion has an active ingredient and the active ingredient is suitable for use in at least one of oral indication, diagnosis, or treatment of a patient.

11. A dental release agent receptacle, comprising:
    an outer portion including a bottom surface configured to be coupled to an outer surface of an individual tooth aperture of an appliance, the bottom surface configured to have a perimeter smaller than a perimeter of the outer surface of the individual tooth aperture and shaped to follow the contours of the outer surface of the individual tooth aperture;
    an inner portion encapsulated within the outer portion; and
    one or more apertures through a top surface of the outer portion of the release agent receptacle allowing for fluid communication from the inner portion and out of the dental release agent receptacle, wherein the top surface is smaller than the bottom surface, and wherein the inner portion and the outer portion are in fluid communication by the one or more apertures only.

12. The dental release agent receptacle of claim 11, wherein the one or more apertures are provided through the outer portion that is shaped to follow the contours of the outer surface of the individual tooth aperture.

13. The dental release agent receptacle of claim 11, wherein the one or more apertures are provided through a portion of the inner portion.

14. The dental release agent receptacle of claim 11, wherein the release agent receptacle provides an indication by demonstrating a change in at least one characteristic of an active ingredient provided as part of the inner portion.

15. The dental release agent receptacle of claim 14, wherein the changed characteristic is selected from the group of characteristics including a color, a shape, and a size of the inner portion.

16. A dental release agent receptacle of claim 14, where the change in the characteristic is provided by interaction of the active ingredient and at least one of moisture, temperature, a chemical, and a biological agent.

17. A dental release agent receptacle of claim 14, where the change in characteristic occurs due to a reaction between the active ingredient and one or more oral fluids.

18. The dental release agent receptacle of claim 11, wherein the one or more apertures are sized based on characteristics of a release of an active ingredient from the inner portion.

19. The dental release agent receptacle of claim 18, wherein the characteristic includes at least one of an amount, a speed, and a direction of the release of the active ingredient from the inner portion.

20. The dental release agent receptacle of claim 11, wherein an active ingredient is located in the inner portion and the active ingredient is released through dissolution.

* * * * *